United States Patent [19]

Angelucci et al.

[11] Patent Number: 5,412,081

[45] Date of Patent: * May 2, 1995

[54] NEW 4'-EPI-4'-AMINO ANTHRACYCLINES

[75] Inventors: Francesco Angelucci; Alberto Bargiotti, both of Milan; Daniela Faiardi, Pavia; Stefania Stefanelli; Antonino Suarato, both of Milan, all of Italy

[73] Assignee: Farmitalia Carlo Erba S.R.L., Milan, Italy

[ * ] Notice: The portion of the term of this patent subsequent to Jan. 22, 2008 has been disclaimed.

[21] Appl. No.: 1,229

[22] Filed: Jan. 6, 1993

Related U.S. Application Data

[63] Continuation-in-part of Ser. No. 730,933, Jul. 29, 1991, abandoned.

[30] Foreign Application Priority Data

Feb. 7, 1989 [GB] United Kingdom ............... 8902709
Feb. 2, 1990 [WO] WIPO ............... PCT/EP90/00183

[51] Int. Cl.[6] ............................................. C07H 15/24
[52] U.S. Cl. ............................................. 536/6.4
[58] Field of Search ............................ 536/6.4; 514/34

[56] References Cited

U.S. PATENT DOCUMENTS

| | | | |
|---|---|---|---|
| 4,348,388 | 9/1982 | Garland et al. | 536/6.4 |
| 4,563,444 | 1/1986 | Angelucci et al. | 536/6.4 |
| 4,697,005 | 9/1987 | Swenton et al. | 536/6.4 |
| 4,749,693 | 6/1988 | Angelucci et al. | 514/34 |
| 4,891,360 | 1/1990 | Angelucci et al. | 514/34 |
| 4,965,351 | 10/1990 | Caruso et al. | 536/6.4 |
| 4,987,126 | 1/1991 | Bargiotti et al. | 514/34 |

FOREIGN PATENT DOCUMENTS

| | | |
|---|---|---|
| 0051280 | 5/1982 | European Pat. Off. . |
| 0328400 | 8/1989 | European Pat. Off. . |
| 2454445 | 12/1980 | France ............... 536/6.4 |
| 2091243 | 7/1982 | United Kingdom . |

OTHER PUBLICATIONS

Biomedical and Environmental Mass Spec., vol. 13, 1986, John Wiley & Sons Ltd, C. Monneret et al.: "Desorption chemical ionization mass spectrometry of anthracyclines and of trisaccharides related to Aclacinomycin A and arcellomycin", pp. 319–326.

Primary Examiner—Douglas W. Robinson
Assistant Examiner—Elli Peselel
Attorney, Agent, or Firm—Oblon, Spivak, McClelland, Maier, & Neustadt

[57] ABSTRACT

Anthracycline glycosides having the general formula 1 and 2:

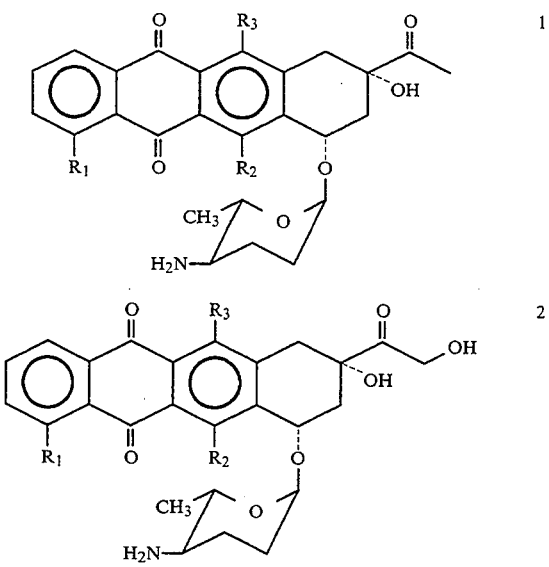

wherein $R_1$ is selected from the group consisting of hydrogen, fluorine, hydroxy or amino; $R_2$ and $R_3$ represent hydroxy or one of $R_2$ and $R_3$ is a hydrogen atom, a nitro or an amino group and the other of $R_2$ and $R_3$ is a HYDROXY group, exhibit activity against LoVo and LoVo/Dx in vitro.

5 Claims, No Drawings

NEW 4′-EPI-4′-AMINO ANTHRACYCLINES

This application is a continuation of application Ser. No. 07/730,933, filed on Jul. 29, 1991, now abandoned.

The present invention relates to a new class of anthracycline glycosides having antitumour activity in vitro, methods for their preparation, and pharmaceutical compositions containing them. The invention also relates to the preparation of certain novel intermediates.

The invention provides anthracycline glycosides having the general formulae 1 and 2:

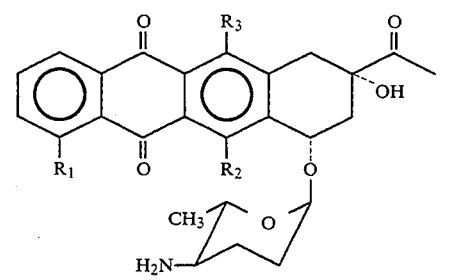

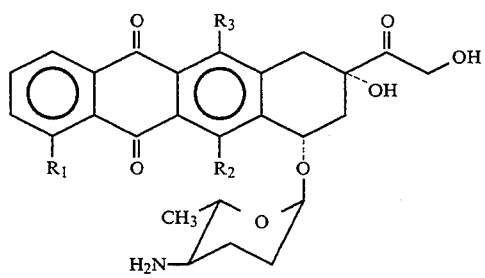

wherein $R_1$ is selected from the group consisting of hydrogen, fluorine, hydroxy and amino; $R_2$ and $R_3$ both represent hydroxy or one of $R_2$ and $R_3$ is hydrogen, nitro or amino and the other of $R_2$ and $R_3$ is hydroxy; and pharmaceutically acceptable salts thereof. Preferred salts are the hydrochloride salts.

The anthracycline glycosides of the general formulae 1 and 2 include:
4-demethyl-3′-deamino-4′-deoxy-4′-epi-amino-daunorubicin (1a: $R_1=R_2=R_3=OH$)
4-demethyl-3′-deamino-4′-deoxy-4′-epi-amino-doxorubicin (2a: $R_1=R_2=R_3=OH$)
4-demethoxy-4-amino-3′-deamino-4′-deoxy-4′-epi-amino-daunorubicin (1b: $R_1=NH_2$, $R_2=R_3=OH$)
4-demethoxy-4-amino-3′-deamino-4′-deoxy-4′-epi-amino-doxorubicin (2b: $R_1=NH_2$, $R_2=R_3=OH$)
4-demethoxy-4-fluoro-3′-deamino-4′-deoxy-4′-epi-amino-daunorubicin (1c: $R_1=F$, $R_2=R_3=OH$)
4-demethoxy-4-fluoro-3′-deamino-4′-deoxy-4′-epi-amino-doxorubicin (2c: $R_1=F$, $R_2=R_3=OH$)
4-demethyl-6-deoxy-3′-deamino-4′-deoxy-4′-epi-amino-daunorubicin (1d: $R_1=R_3=OH$, $R_2=H$)
4-demethyl-6-deoxy-3′-deamino-4′-deoxy-4′-epi-amino-doxorubicin (2d: $R_1=R_3=OH$, $R_2=H$)
4-demethoxy-11-deoxy-11-nitro-3′-deamino-4′-deoxy-4′-epi-amino-daunorubicin (1e: $R_1=H$, $R_2=OH$, $R_3=NO_2$)
4-demethoxy-11-deoxy-11-nitro-3′-deamino-4′-deoxy-4′-epi-amino-doxorubicin (2e: $R_1=H$, $R_2=OH$, $R_3=NO_2$)
4-demethoxy-6-deoxy-6-nitro-3′-deamino-4′-deoxy-4′-epi-amino-daunorubicin (1f: $R_1=H$, $R_2=NO_2$, $R_3=OH$)
4-demethoxy-6-deoxy-6-nitro-3′-deamino-4′-deoxy-4′-epi-amino-doxorubicin (2f: $R_1=H$, $R_2=NO_2$, $R_3=OH$)
4-demethoxy-11-deoxy-11-amino-3′-deamino-4′-deoxy-4′-epi-amino-daunorubicin (1g: $R_1=H$, $R_3=NH_2$, $R_2=OH$)
4-demethoxy-11-deoxy-11-amino-3′-deamino-4′-deoxy-4′-epi-amino-doxorubicin (2g: $R_1=H$, $R_3=NH_2$, $R_2=OH$)
4-demethoxy-6-deoxy-6-amino-3′-deamino-4′-deoxy-4′-epi-amino-daunorubicin (1h: $R_1=H$, $R_2=NH_2$, $R_3=OH$)
4-demethoxy-6-deoxy-6-amino-3′-deamino-4′-deoxy-4′-epi-amino-doxorubicin (2h: $R_1=H$, $R_2=NH_2$, $R_3=OH$)

The new anthracycline glycoside antibiotics of the invention, i.e. those of formula 1 and 2, are condensation products of (a) aglycones of general formula 3 or 6:

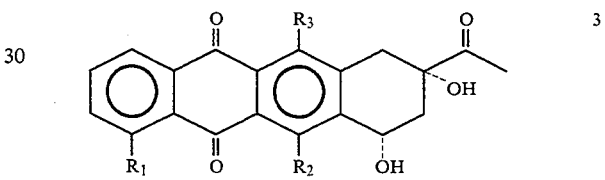

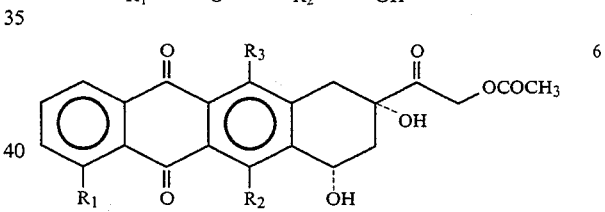

wherein $R_1$, $R_2$ and $R_3$ are as defined above with proviso that neither $R_2$ nor $R_3$ is an amino group and (b) a protected halosugar of the formula 4:

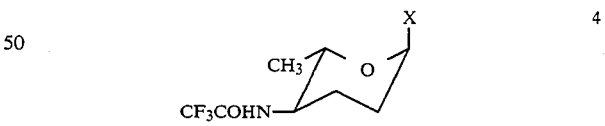

wherein X is a halogen, preferably chlorine.

The synthetic methods for the preparation of the above mentioned anthracyclines follows two methods: Method A is depicted in Scheme I and involves the use of the aglycone of formula 3, and Method B, which is shown in Scheme II and involves the use of the aglycone of formula 6. The preparation of the C-6 or C-11 amino compounds of formula 2 is illustrated in Scheme III.

Scheme I

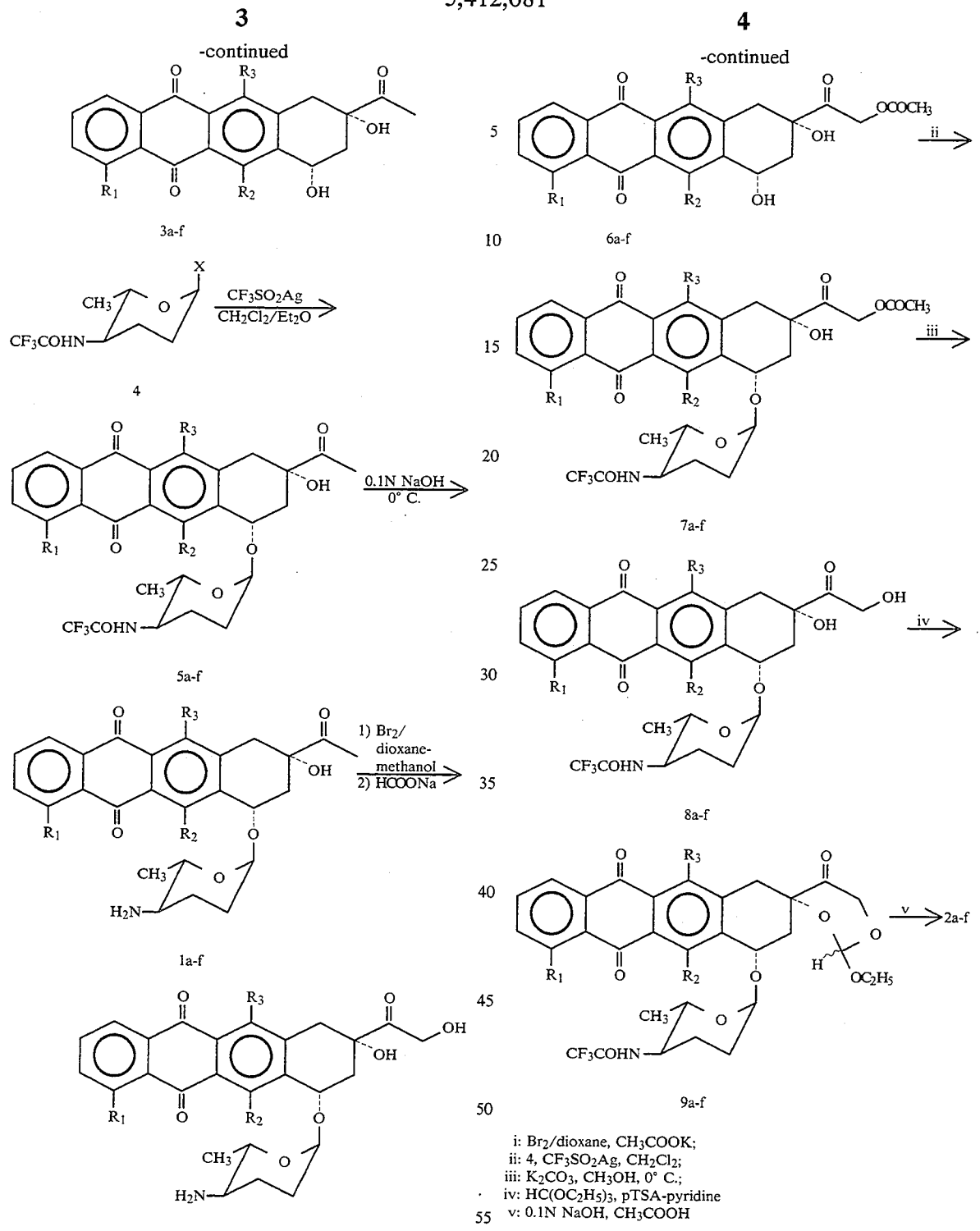
i: $Br_2$/dioxane, $CH_3COOK$;
ii: 4, $CF_3SO_2Ag$, $CH_2Cl_2$;
iii: $K_2CO_3$, $CH_3OH$, 0° C.;
iv: $HC(OC_2H_5)_3$, pTSA-pyridine
v: 0.1N NaOH, $CH_3COOH$
Scheme II
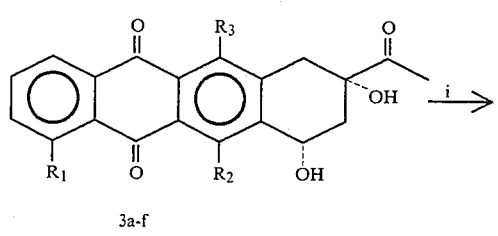
Scheme III
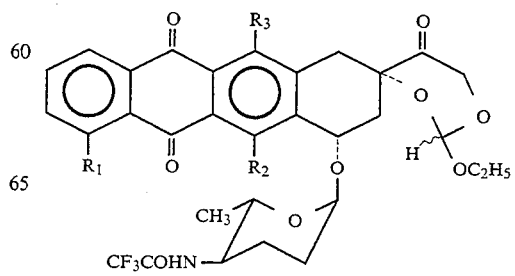

-continued

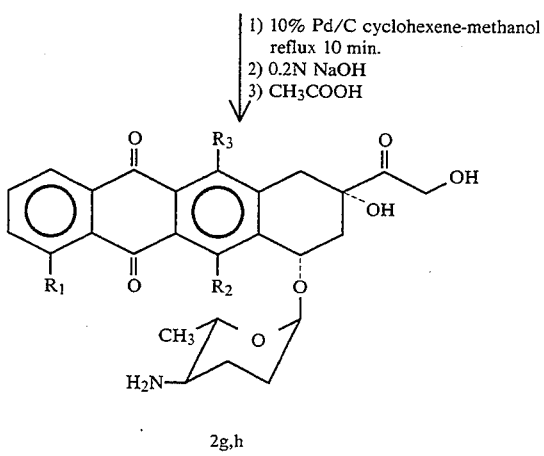

9e,f

Method A

The present invention provides a process for the preparation of an anthracycline glycoside of formula 1 or 2 as defined above with proviso that for a glycoside of formula 2 neither $R_2$ nor $R_3$ is an amino group, or a pharmaceutically acceptable acid addition salt thereof, which process comprises:

(i) condensing an aglycone of formula 3:

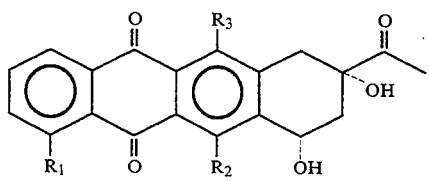

wherein $R_1$, $R_2$ and $R_3$ are as defined above except that neither $R_2$ nor $R_3$ is an amino group, with a 1-halo-2,3,4,6-tetradeoxy-4-(N-trifluoroacetamido)-L-erythro-hexopyranoside of formula 4:

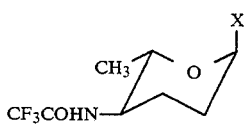

wherein X is halogen;

(ii) removing the N-trifluoroacetyl group from the compound of formula 5 thus obtained:

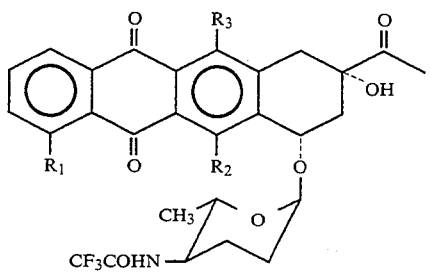

wherein $R_1$, $R_2$ and $R_3$ are as defined in step (i), so as to obtain a said anthracycline glycoside of formula 1 except that neither $R_2$ nor $R_3$ is an amino group;

(iii) if desired, converting the said glycoside of formula 1 obtained in step (ii) into a pharmaceutically acceptable acid addition salt thereof;

(iv) if desired, reducing a said glycoside of formula 1 wherein one of $R_2$ and $R_3$ is a nitro group obtained in step (ii) or a said salt thereof obtained in step (iii) so as to obtain a said glycoside of formula 1 wherein one of $R_2$ and $R_3$ is an amino group and, if desired, converting the said glycoside of formula 1 wherein one of $R_2$ and $R_3$ is an amino group into a pharmaceutically acceptable acid addition salt thereof;

(v) if desired, brominating the said glycoside of formula 1 obtained in step (ii) or pharmaceutically acceptable acid addition salt thereof obtained in step (iii) and hydrolysing the 14-bromo derivative thus obtained to form a corresponding anthracycline glycoside of formula 2 as defined above; and (vi) if desired, converting the said glycoside of formula 2 into a pharmaceutically acceptable acid addition salt thereof.

This procedure allows the preparation of anthracycline glycosides from the corresponding aglycones 3 and a protected halosugar 4. The procedure is similar to that described in U.S. Pat. No. 4,107,423. The coupling product is hydrolyzed to a daunorubicin derivative 1 and can be converted to the corresponding doxorubicin derivative 2 in accordance with the method described in U.S. Pat. No. 3,803,124.

The starting materials for the reaction sequences of Scheme I are the well known 4-demethyldaunomycinone (3a:$R_1$=$R_2$=$R_3$=OH), the aglycone 4-demethoxy-4-amino-daunomycinone (3b:$R_1$=NH$_2$, $R_2$=$R_3$=OH) (EP-A-0288268), 4-demethoxy-4-fluorodaunomycinone (3c: $R_1$=F, $R_2$=$R_3$=OH) [G. W. Morrow and J. Swenton, J. Org. Chem.; 52, 713, 1987] and 4-demethyl-6-deoxydaunomycinone (3d: $R_1$=$R_3$=OH, $R_2$=H) [U.S. Pat. No. 4,600,537]. The C-11 and C-6 nitro aglycones 4-demethoxy-11-deoxy-11-nitrodaunomycinone (3e: $R_1$=H, $R_2$=OH, $R_3$=NO$_2$) and 4-demethoxy-6-deoxy-6-nitrodaunomycinone (3f: $R_1$=H, $R_2$=NO$_2$, $R_3$=OH) both described in U.S. Pat. No. 4,749,693.

An aglycone of formula 3 is generally reacted at room temperature in step (i) with a compound of formula 4 in the presence of a molecular sieve and silver trifluoromethanesulphonate to form one of the N-trifluoroacetyl glycosides 5a-f. Compounds of formula 1a-f are obtained by removing the amino protecting group by mild alkaline hydrolysis. Preferably in step (ii) the compound of formula 5, dissolved in acetone, is submitted, at a temperature of 0° C. and for one hour, to mild alkaline hydrolysis with 0.2N aqueous sodium hydroxide to give a said glycoside of formula 1. Treatment with methanolic hydrogen chloride yields the hydrochloride.

In step (iv), typically reduction is effected by treatment with Pd/C, for example 10% Pd/C. The nitro glycoside of formula 1 or salt thereof may therefore be refluxed in a mixture of methanol and cyclohexene in the presence of 10% Pd/C for ten minutes. The resulting amino glycoside of formula 1 can be isolated as its hydrochloride as above.

Preferably the said glycoside of formula 1, dissolved in a mixture of anhydrous methanol and dioxane, is treated in step (v) with a chloroform solution of bromine to afford the corresponding 14-bromo derivative which is hydrolyzed for two days at room temperature with an aqueous solution of sodium formate to give a said glycoside of formula 2 as the free base and in step (vi) the said glycoside of formula 2 is isolated as its hydrochloride. Isolation of the glycoside of formula 2 as the hydrochloride is typically achieved by treating the glycoside with methanolic hydrogen chloride.

According to an embodiment of this process 4-deme-thyldaunomycinone (3a), dissolved in dry methylene chloride, is reacted at room temperature for one hour with 1-chloro-2,3,4,6-tetradeoxy-4-(N-tri-fluoroacetamido)-L-erythro-hexopyranoside (4) in presence of molecular sieves and silver trifluoromethanesulphonate to obtain the N-protected glycoside 5a which, dissolved in acetone, is submitted at a temperature of 0° C. and for one hour, to a mild alkaline hydrolysis with 0.2N aqueous sodium hydroxide to give the compound of formula 1a as a free base which, by treatment with anhydrous methanolic hydrogen chloride is isolated as its hydrochloride.

If desired, 1a is reacted with bromine in methylene chloride to obtain its 14-bromo derivative from which, after hydrolysis at room temperature and for 48 hours under nitrogen with an aqueous solution of sodium formate, the compound of formula 2a is obtained as free base and, by treatment with anhydrous methanolic hydrogen chloride, is isolated as its hydrochloride.

Method B

The invention provides a process for the preparation of an anthracycline glycoside of formula 2 as defined above, with the proviso that neither $R_2$ nor $R_3$ is an amino group, or a pharmaceutically acceptable acid addition salt thereof, which process comprises:

(i') condensing a 14-protected aglycone of formula 6:

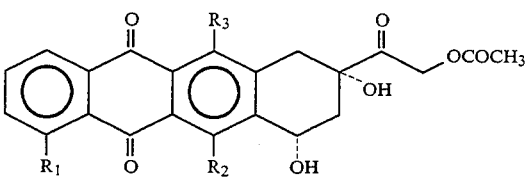

wherein $R_1$, $R_2$ and $R_3$ are as defined above except that neither $R_2$ nor $R_3$ is an amino group, with a 1-halo-2,3,4,6-tetradeoxy-4-(N-trifluoroacetamido)-L-erythro-hexopyranoside of formula 4 as defined above;

(ii') removing the 14-protecting group from the resulting N-protected glycoside of formula 7:

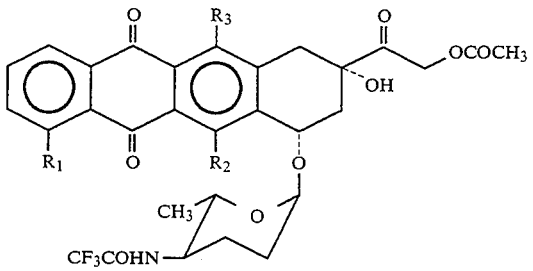

wherein $R_1$, $R_2$ and $R_3$ are as defined above, to give the compound of formula 8:

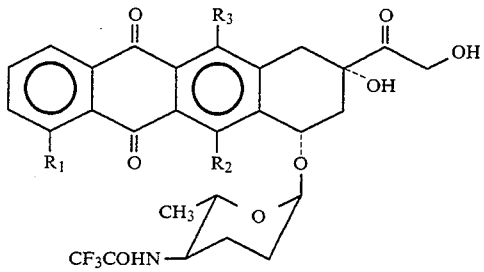

wherein $R_1$, $R_2$ and $R_3$ are as defined above;

(iii') converting the compound of formula 8 into a 9,14-orthoformate derivative of formula 9:

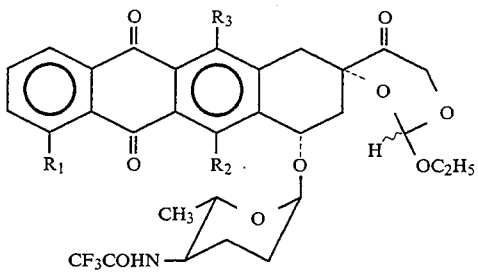

wherein $R_1$, $R_2$ and $R_3$ are as defined above;

(iv') removing the N-trifluoroacetyl group and the orthoformate protecting group to obtain a said glycoside of formula 2; and (v') if desired, converting the said glycoside of formula 2 into a pharmaceutically acceptable acid addition salt thereof.

This procedure allows the preparation of anthracycline glycosides of general formula 2 by coupling (a) the corresponding 14-hydroxylated and protected aglycones and (b) a protected halosugar 4. The procedure is similar to that described in U.S. Pat. No. 4,107,423. In Scheme II is depicted the route to doxorubicin derivatives 2a–f. The starting materials are the aglycones 3a–f suitably functionalized and protected in the side chain as 14-acetoxy derivatives.

Typically in step (i') the aglycone of formula 6 is reacted at room temperature with a 1-chloro-hexapyranoside of formula 4 in the presence of a molecular sieve and silver trifluoromethansulfonate. Preferably in step (ii') the compound of formula 7 is treated at 0° C., for four hours and under a nitrogen atmosphere with potassium carbonate. Generally in step (iii') the compound of formula 8 is treated with triethyl orthoformate, for example in methylene chloride and in the presence of pyridinium p-toluensulfonate for one hour at room temperature.

Preferably in step (iv') the compound of formula 9 is subjected to mild alkaline aqueous hydrolysis to remove the N-trifluoroacetyl group and is treated with acetic acid to remove the orthoformate protecting group to obtain the said glycoside of formula 2 as a free base which, in step (v'), is treated with anhydrous methanolic hydrogen chloride to isolate the glycoside as its hydrochloride salt.

More particularly in one embodiment 4-demethoxy-11-deoxy-11-nitrodaunomycinone (3d: $R_1$=H, $R_2$=OH, $R_3$=NO$_2$) is dissolved in dry dioxane and treated with a solution of bromine in methylene chloride for two hours at room temperature, then precipitated with hexane. The residue, dissolved in acetone, is added with potassium acetate and stirred for one hour to give the acetoxy derivative 6d. This compound is dissolved in dry methylene chloride and reacted with 1-chloro-2,3,4,6-tetradeoxy-4-(N-trifluoroacetamido)-L-erythro-hexopyranoside (4) as described above to give the protected 14-acetoxy-N-trifluoroacetyl glycoside 7d.

In order to remove the protecting groups, compound 7d is first dissolved in methanol and treated with potassium carbonate for four hours at 0° C. under nitrogen to give 8d, then is treated with triethyl orthoformate in methylene chloride and in the presence of pyridinium p-toluensulfonate for one hour at room temperature to give the 9,14-orthoformate derivative 9e. This is subjected to mild alkaline aqueous hydrolysis to remove the N-protecting group and finally treated with acetic acid to remove the orthoformate protecting group and give compound 1e as free base which, by treatment with anhydrous methanolic hydrogen chloride, is isolated as its hydrochloride.

The present invention also provides a process for the preparation of an anthracycline glycoside of formula 2 above wherein $R_1$ is as defined above and one of $R_2$ and $R_3$ is hydroxy and the other of $R_2$ and $R_3$ is an amino group, or a pharmaceutically acceptable acid addition salt thereof, which process comprises:

(i″) reducing the C-6 or C-11 nitro group of a 9,14-orthoformate derivative of formula 9 as defined above wherein one of $R_2$ and $R_3$ is hydroxy and the other of $R_2$ and $R_3$ is a nitro group;

(ii″) removing the N-trifluoroacetyl group and the orthoformate protecting group from the C-6 or C-11 amino group-containing compound thus formed to obtain a said glycoside of formula 2; and (iii″) if desired, converting the said glycoside of formula 2 into a pharmaceutically acceptable acid addition salt thereof.

Scheme III shows the route to C-6 and C-11 amino anthracyclines of formula 2 starting from the corresponding C-6 and C-11 protected nitro glycosides. The 9,14-orthoformate nitro derivatives 9e or 9f may be converted respectively to amino glycosides 2g or 2h by refluxing the nitro compounds in a mixture of methanol and cyclohexene in the presence of 10% Pd/C for ten minutes, and removing the N-trifluoroacetyl group in a basic medium, for example as described above for Method A or Method B, and the orthoformate protecting group with acetic acid. The compounds 2g and 2h may be converted into their respective hydrochloride salts by treatment with anhydrous methanolic hydrogen chloride.

As is apparent from the foregoing, the processes of the invention involve the preparation and use of several novel intermediates. These too are within the scope of the present invention, more especially the compounds of formulae 5 and 7 to 9.

The invention also provides pharmaceutical compositions comprising an anthracycline glycoside of formula 1 or 2 or a pharmaceutically acceptable acid addition salt thereof, together with a pharmaceutically acceptable carrier or diluent. Conventional carriers and diluents may be used. The composition may be formulated and administered in conventional manner.

The compounds of the invention are useful in methods of treatment of the animal body by therapy.

The biological activity of the compounds according to the invention was tested in vitro against LoVo (human colon adenocarcinoma) and LoVo/DX cells in comparison with doxorubicin and 4-demethoxydaunorubicin (4-dem-DNR). The results are shown in Table 1.

TABLE 1

| | in vitro activity | | |
|---|---|---|---|
| | Cytotoxicity after 4h of treatment ($IC_{50}^1$ = ng/ml) | | |
| Compounds | LoVo | LoVo/DX | R.I.[2] |
| Doxorubicin | 60 | 2180 | 36 |
| 4-dem-DNR | 20 | 125 | 6 |
| 1a | 1.1 | 2.7 | 2.4 |
| 1c | 1.2 | 6.0 | 5.0 |
| 1h | 4.0 | 8.6 | 2.2 |
| 2d | 1.2 | 3.8 | 3.2 |
| 2e | 48.4 | 205 | 4.2 |
| 2f | 116 | 2256 | 19.4 |
| 2g | 18.8 | 109 | 5.8 |
| 2h | 6.2 | 90 | 14.2 |

[1] $IC_{50}$ = concentration inhibiting by 50% colony growth
[2] R.I. = Resistance Index = ($IC_{50}$ LoVo/DX)/($IC_{50}$ LoVo)

The following Examples illustrate the invention

EXAMPLE 1

Preparation of 4-demethyl-3′-deamino-4′-deoxy-4′-epi-amino-daunorubicin hydrochloride (1a)

0.76 g (2 mmole) of 4-demethyldaunomycinone (3a) was dissolved with 300 ml of anhydrous methylene chloride in the presence of molecular sieves (4 Å). The mixture was cooled at 10° C., bubbled with nitrogen and added dropwise, under stirring, with 0.86 g (3.2 mmole) of 1-chloro-2,3,4,6-tetradeoxy-4-(N-trifluoroacetamido)-L-erythro-hexopyranoside (4) dissolved in 40 ml of anhydrous methylene chloride and 0.78 g (3.0 mmole) of silver trifluoromethanesulphonate dissolved in 40 ml of diethyl ether. After twenty minutes the reaction mixture was treated with 30 ml of aqueous saturated sodium hydrogen carbonate and filtered off. The organic layer was washed with water, dried over anhydrous sodium sulphate and the solvent was removed in vacuo. The residue was chromatographed over a silica gel column using a mixture of methylene chloride acetone (98:2 by volume) to give 0.8 g of 4-demethyl-3′-deamino-4′-deoxy-4′-epi-N-trifluoroacetyldaunorubicin (5a). The trifluoroacetyl protecting group was removed by dissolving compound 5a in acetone and treating with aqueous 0.2N sodium hydroxide at 0° C. After one hour the solution was adjusted to pH 8.1 and extracted repeatedly with methylene chloride. The combined organic extracts, after being dried and concentrated to a small volume were acidified to pH 3.5 with anhydrous methanolic hydrogen chloride. Upon addition of diethyl ether there was obtained 0.64 g (yield 54%) of the title compound 1a as hydrochloride salt. m.p. 168°–169° C. (with dec.). TLC on Kieselgel Plate (Merck F$_{254}$) solvent system: methylene chloride/methanol/acetic acid/water (80:20:7:3 by volume) Rf:0.73. MS-FD: [M]+ 497.

[1] HNMR (200 MHz, DMSO-d$_6$) δ: 1.21 (d, J=6.2 Hz, 3H, 5′CH$_3$), 1.6–1.8 (m, 4H, 2′-CH$_2$, 3′CH$_2$), 2.1–2.3 (m, 2H, 8-CH$_2$), 2.27 (s, 3H, COCH$_3$), 2.85 (m, 1H, 4′-H), 2.95 (m, 2H, 10-CH$_2$), 4.11 (dq, J=6.2, 9.9 Hz, 1H, 5′-H), 4.98 (m, 1H, 7-H), 5.22 (s, 1H, 9-OH), 7.40 (dd, J=2.0, 7.5 Hz, 1H, 3-H) 7.82 (m, 2H, 1-H, 2-H), 8.10 (bs, 3H, 4'-NH$_3$+), 11.96 (s, 1H, 11-OH), 12.87 (s, 1H, 6-OH), 13.40 (s, 1H, 4-OH)

EXAMPLE 2

Preparation of 4-demethoxy-4-amino-3'-deamino-4'-deoxy-4-epi-amino-daunorubicin hydrochloride (1b)

0.38 g (1 mmole) of 4-demethoxy-4-aminodaunomycinone (3b) was coupled with 0.37 g (1.5 mmole) of 1-chloro-2,3,4,6-tetradeoxy-4-(N-trifluoroacetamido)-L-erythro-hexopyranoside (4) following the procedure described in Example 1 to afford 0.35 g (yield 60%) of the title compound 1b as hydrochloride salt. TLC on Kieselgel Plate (Merck F$_{254}$) solvent system: methylene chloride/methanol/acetic acid/water (80:20:7:3 by volume) Rf:0.45

$^1$HNMR (200 MHz, DMSO-d$_6$) δ (inter alia): 2.27 (s, 3H, COCH$_3$), 2.85 (m, 1H, 4'-H), 4.98 (m, 1H, 7-H), 6.80 (bd, 2H, 4-NH$_2$), 6.93 (d, J=8.0 Hz, 1H, 3-H), 7.46 (t, J=8.0 Hz, 1H, 2-H), 7.64 (d, J=8.0 Hz, 1H, 1-H), 8.10 (bs, 3H, 4'-NH$_3$+), 13.52 (s, 1H, 11-OH), 14.00 (s, 6-OH)

EXAMPLE 3

Preparation of 4-demethoxy-4-fluoro-3'-deamino-4'-deoxy-4'-epi-amino-daunorubicin hydrochloride (1c)

0.38 g (1 mmole) of 4-demethoxy-4-fluorodaunomycinone (3c) was coupled with 0.37 g (1.5 mmole) of 1-chloro-2,3,4,6-tetradeoxy-4-(N-trifluoroacetamido)-L-erythro-hexopyranoside (4) following the procedure described in Example 1 to afford 0.48 g of N-trifluoroacetyl derivative 5c.

After removal of the N-protecting group, following standard procedure, was obtained 0.40 g (yield 74%) of the title compound 1c. TLC on Kieselgel Plate (Merck F$_{254}$) solvent system: methylene chloride/methanol/acetic acid/water (80:20:7:3 by volume) Rf:0.68, m.p. 158°–159° C. (with dec.)

EXAMPLE 4

Preparation of 4-demethyl-3'-deamino-4'-deoxy-4'-epi-amino-doxorubicin hydrochloride (2a)

0.3 g (0.6 mmole) of 4-demethyl-3'-deamino-4'-deoxy-4'-epi-aminodaunorubicin (1a) was dissolved in a mixture of anhydrous methanol and dioxane and added with 1.2 ml of a solution containing 9 g of bromine in 100 ml of methylene chloride, according to the method described in U.S. Pat. No. 3,803,124, to afford the 14-bromo derivative, which was dissolved in 20 ml of acetone and treated with 0.4 g of sodium formate dissolved in 2 ml of water. The reaction mixture was stirred at room temperature for two days, then water was added and extracted with methylene chloride. After standard work up, the resulting red solution was concentrated to small volume under vacuum, adjusted to pH 3.5 with anhydrous methanolic hydrogen chloride, then added with an excess of diethyl ether to give 0.2 g, (yield 75%), of the title compound 2a as hydrochloride. TLC on Kieselgel Plate (Merck F$_{254}$) solvent system: methylene chloride/methanol/acetic acid/water (80:20:7:3 by volume) Rf:0.60

EXAMPLE 5

Preparation of 4-demethyl-6-deoxy-14-acetyl-adriamycinone (6d)

To a solution of 0.85 g (2.3 mmole) of 4-demethyl-6-deoxydaunomycinone (3d), dissolved in 150 ml of anhydrous dioxane, was added 4.6 ml of solution containing 9 g of bromine in 100 ml of methylene chloride. The mixture was left at room temperature for two hours, after that the bromo derivative was precipitated by adding n-hexane and collected. The residue was dissolved with 300 ml of acetone and added under stirring with 2.7 g of potassium acetate. After one hour the reaction mixture was diluted with methylene chloride and washed with water. The organic layer was dried over anhydrous sodium sulphate, filtered off and the solvent was removed under reduced pressure. The residue was chromatographed on a column of silica gel to give 0.75 g (yield 76%) of the title compound 6d. TLC on Kieselgel Plate (Merck F$_{254}$) solvent system methylene chloride/acetone (95:5 by volume) Rf:0.13

EI-MS: [M]+ 426

$^1$HNMR (200 MHz, DMSO d$_6$) δ: 1.88 (dd, J=9.3, 13.1 Hz, 1H, 8ax-H), 2.06 (s, 3H, COCH$_3$), 2.41 (dd, J=5.7, 13.1 Hz, 1H, 8e-H), 2.76–3.04 (two d, J=18.6 Hz, 10-CH$_2$), 4.57 (m, 1H, 7-H), 5.09–5.23 (two d, J=17.8 Hz, 2H, COCH$_2$OCO), 5.89 (d, J=6.6 Hz, 1H, 7-OH), 6.10 (s, 1H, 9-OH), 7.39 (dd, J=1.5, 7.9 Hz, 1H, 3-H), 7.7–7.9 (m, 2H, 1-H, 2-H), 7.90 (s, 1H, 6-H), 12.60–12.90 (two bs, 2H, 4-OH, 11-OH).

EXAMPLE 6

Preparation of 4-demethyl-6-deoxy-3'-deamino-4'-deoxy-4'-epi-N-trifluoacetyl-doxorubicin (8d)

0.61 g (1.43 mmole) of 4-demethyl-6-deoxy-14-acetyl-adriamycinone (6d) was dissolved with 250 ml of anhydrous methylene chloride and 150 ml of anhydrous tetrahydrofurane. The mixture was cooled at 10° C., bubbled with nitrogen and added dropwise, under stirring, with 1 g (4 mmole) of 1-chloro-2,3,4,6-tetradeoxy-4-(N-trifluoroacetamido)-L-erythro-hexopyranoside (4) dissolved in 50 ml of anhydrous methylene chloride and 1 g (4 mmole) of silver trifluoromethanesulphonate dissolved in 50 ml of diethyl ether. After twenthy minutes the reaction mixture was treated with 20 ml of aqueous saturated sodium hydrogen carbonate and filtered off. The organic layer was washed with water, dried over anhydrous sodium sulphate and the solvent was removed in vacuo. The residue was chromatographed over a silica gel column to give 0.4 g (yield 44%) of 4-demethyl-6-deoxy-14-acetyl-3'-deamino-4'-deoxy-4'-epi-N-trifluoroacetyldoxorubicin (7d). TLC on Kieselgel Plate (Merck F$_{254}$) solvent system methylene chloride/acetone (9:1 by volume) RF:0.45 FD-MS: [M]+ 636

$^1$HNMR (200 MHz, DMSO d$_6$) δ, (inter alia): 1.06 (d, J=6.0 Hz, 3H, 5'-CH$_3$), 1.6–2.0 (m, 5H, 8ax-H, 2'-CH$_2$, 3'-CH$_2$), 2.05 (s, 3H, COCH$_3$) 3.56 (m, 1H, 4'-H), 3.93 (m, 1H, 5'-H), 5.14 (m, 2H, COCH$_2$OCO), 5.17 (m, 1H, 1'-H), 9.37 (bd, J=8.6 Hz, 1H, NHCOCF$_3$), 12.45, 12.91 (two s, 2H, 4-OH, 11-OH).

Compound 7d was dissolved with 200 ml of methanol, treated at 0° C. with 2 ml of a 10% aqueous solution of potassium carbonate and left to stand for four hours at 0° C. under nitrogen.

The solution was neutralized with acetic acid, diluted with water and the product extracted with methylene chloride. After silica gel filtration 0.25 g of the title compound 8d was recovered (yield 89%). TLC on Kieselgel Plate (Merck F$_{254}$) solvent system: methylene chloride/acetone (9:1 by volume) Rf:0.26. FD-MS: [M]+ 593.

EXAMPLE 7

Preparation of 4-demethyl-6-deoxy-3'-deamino-4'-deoxy-4'-epi-amino-doxorubicin, hydrochloride (2d)

0.2 g (0.33 mmole) of product 8d, prepared as described in Example 6, was dissolved with 60 ml of dry methylene chloride and added with 15 ml of triethyl orthoformate and 0.1 g of pyridinium p-toluensulfonate. After one hour the solution was washed with water, dried over anhydrous sodium sulphate and reduced to small volume under reduced pressure. The solution was poured into n-hexane and the precipitate of 9,14-orthoformate derivative 9d was collected by filtration. TLC on Kieselgel Plate (Merck F$_{254}$) solvent system: methylene chloride/acetone (95:5 by volume) Rf:0.7

The residue was dissolved with 200 ml of 0.2N aqueous sodium hydroxide and the solution was left for ten hours at 8° C. under nitrogen. Then the solution was adjusted at pH 8.5 with acetic acid and extracted with methylene cloride. After standard work up, the resulting free base was treated with an aqueous solution of acetic acid for two hours at room temperature. The mixure was brought to pH 8.5 with aqueous sodium hydrogen carbonate and extracted with methylene chloride. The solvent was removed in vacuo and the residue chromatographed on silica gel column to afford 0.12 g (yield 66%) of the title compound as free base which was transformed into the hydrochloride salt 2d by treatment with anhydrous methanolic hydrogen chloride. TLC on Kieselgel Plate (Merck F$_{254}$) solvent system: methylene chloride/methanol/acetic acid/water (80:20:7:3 by volume) Rf:0.52. m.p. 155° C. (dec.) FD-MS: [M]+ 438

$^1$HNMR (200 MHz, DMSO d$_6$) δ: 1.21 (d, J=6.2 Hz, 3H, 5'-CH$_3$), 1.7–2.0 (m, 5H, 8ax-H, 2'-CH$_2$, 3'-CH$_2$), 2.4–2.5 (m, 1H, 8e-H), 2.77, 3.08 (two d, J=17.7 Hz, 2H, 10-CH$_2$), 2.88 (m, 1H, 4'-H), 3.95 (dq, J=6.2, 9.9 Hz, 1H, 5'-H), 4.55 (d, J=5.5 Hz, 2H, CH$_2$OH), 4.76 (m, 1H, 7-H), 4.84 (t, J=5.5 Hz, 1H, CH$_2$OH), 5.20 (m, 1H, 1'-H), 5.93 (s, 1H, 9-OH), 7.40 (dd, J=1.6, 7.7 Hz, 1H, 3-H), 7.7–7.9 (m, 2H, 2-H, 1-H, 7.74 (s, 1H, 6-H).

EXAMPLE 8

Preparation of 4-demethoxy-11-deoxy-11-nitro-14-acetyladriamycinone (6e)

2.3 g (5.7 mmole) of 4-demethoxy-11-deoxy-11-nitro-daunomycinone (3e) was transformed into 1.8 g, (yield 70%), of the compound 6e following the procedure reported in Example 5. TLC on Kieselgel Plate (Merck F$_{254}$) solvent system: methylene chloride/acetone (95:5 by volume) Rf:0.2. FD-MS: [M]+ 455.

$^1$HNMR (200 MHz, CDCl$_3$) δ: 2.11 (ddd, J=1.8, 5.0, 15.0 Hz, 1H, 8ax-H), 2.18 (s, 3H, COCH$_3$), 2.56 (ddd, J=2.2, 2.2, 15.0 Hz, 1H, 8e-H), 2.88 (dd, J=2.2, 18.2 Hz, 1H, 10e-H), 3.18 (d, J=18.2 Hz, 1H, 10ax-H), 3.42 (dd, J=1.8, 3.3 Hz. 1H, 7-OH), 4.68 (s, 1H, 9-OH), 5.04, 5.34 (two d, J=18.2 Hz, 2H, COCH$_2$OCO), 5.42 (m, 1H, 7-H), 7.88 (m, 2H, 2-H, 3-H), 8.29 (m, 2H, 1-H, 4-H), 13.71 (s, 1H, 6-OH).

EXAMPLE 9

Preparation of 4-demethoxy-11-deoxy-11-nitro-9,14-orthoformate-3'-deamino-44'-deoxy-4'-epi-N-trifluoroacetyl-doxorubicin (9e)

1.76 g (3.8 mmole) of product 6e was condensed with 1.3 g (5.2 mmole) of the chloro-sugar 4 in presence of silver trifluoromethanesulphonate, following the procedure described in Example 1, to give 1.13 g (yield 44%) of 14-acetyl-N-trifluoroacetyl-derivative 7e. TLC on Kieselgel Plate (Merck F$_{254}$) solvent system: methylene chloride/acetone (95:5 by volume) Rf:0.37. FD-MS: [M]+ 665

$^1$HNMR (200 MHz, CDCl$_3$) δ: 1.28 (d, J=5.8 Hz, 3H, 5'-CH$_3$), 1.8–1.9 (m, 4H, 2'-CH$_2$, 3'-CH$_2$), 2.10 (dd, J=3.8, 15.0 Hz, 1H, 8ax-H), 2.18 (s, 3H, COCH$_3$), 2.56 (ddd, J=1.6, 1.6, 15.0 Hz, 1H, 8e-H), 2.94 (dd, J=1.6, 18.3 Hz, 1H, 10e-H), 3.19 (d, J=18.3 Hz, 1H, 10ax-H), 3.7–4.1 (m, 2H, 4'-H, 5'-H), 4.94, 5.32 (two d, J=17.8 Hz, 2H, COCH$_2$OCO), 5.40 (m, 2H, 7-H, 1'-H), 6.55 (bd, J=8.6 Hz, 1H, NHC=CF$_3$), 7.87 (m, 2H, 2-H, 3-H), 8.2–8.4 (m, 2H, 1-H, 4-H), 13.70 (s, 1H, 6-OH)

Product 7e was dissolved with 1000 ml of methanol and, after cooling at 0° C., a 10% aqueous solution of sodium carbonate was added under stirring and nitrogen atmosphere. After three hours, the mixture was brought to pH 7 with acetic acid, diluted with water and the product was extracted with methylene chloride following standard procedure. The crude material was crystallized from diethyl ether to give 0.9 g (yield 87%) of compound 4-demethoxy-11-deoxy-11-nitro-3'-deamino-4'-deoxy-4'-epi-N-trifluoroacetyl-doxorubicin (8e) TLC on Kieselgel Plate (Merck F$_{254}$) solvent system: methylene chloride/acetone (95:5 by volume) Rf:0.17. Product 8e was treated with triethylorthoformate in presence of pyridinium p-toluensulfonate as described in Example 7 to give 0.78 g (yield 76%) of the title compound 9e. TLC on Kieselgel Plate (Merck F$_{254}$) solvent system: methylene chloride/acetone (95:5 by volume) Rf:0.48.

EXAMPLE 10

Preparation of 4-demethoxy-11-deoxy-11-nitro-3'-deamino-4'-deoxy-4'-epi-amino-doxorubicin (2e)

Following the procedure described in Example 7, 0.32 g (0.43 mmole) of compound 9e was first hydrolyzed in basic media to remove the N-protecting group then with acetic acid to remove the orthoformate protecting group. Treatment with anhydrous methanolic hydrogen chloride afforded 0.16 g (yield 61%) of the title compound 2e as hydrochloride with TLC on Kieselgel Plate (Merck F$_{254}$) solvent system: methylene chloride/methanol/acetic acid (80:20:1 by volume) Rf:0.30. m.p. 159° C. (dec.) MS-FD: [M]+ 527

$^1$HNMR (200 MHz, DMSO d$_6$, 50° C.) δ: 1.23 (d, J=6.2 Hz, 3H, 5'-CH$_3$), 1.7–1.9 (m, 4H, 2'-CH$_2$, 3'-CH$_2$), 2.26 (m, 2H, 8-CH$_2$), 2.82 (m, 2H, 10-CH$_2$), 2.84 (m, 1H, 4'-H), 4.16 (dq, J=6.2, 9.5 Hz, 1H, 5'-H), 4.4–4.7 (m, 3H, COCH$_2$OH, COCH$_2$OH), 5.08 (m, 1H, 7-H), 5.24 (m, 1H, 1'-H), 5.53 (s, 1H, 9-OH), 7.98 (m, 2H, 2-H, 3-H), 8.1–8.3 (m, 2H, 1-H, 4-H).

EXAMPLE 11

Preparation of
4-demethoxy-11-deoxy-11-amino-3'-deamino-4'-deoxy-4'-epi-amino-doxorubicin hydrochloride (2g)

0.32 g (0.43 mmole) of 4-demethoxy-11-deoxy-11-nitro-9,14-ethyl-orthoformate-3'-deamino-4'-deoxy-4'-epi-N-trifluoroacetyldoxorubicin (9e), prepared as described in Example 9, was dissolved in 200 ml of methanol and added with 20 ml of cyclohexene and 0.2 g of 10% Pd/C, under stirring. The mixture was refluxed for ten minutes, then cooled at room temperature and the catalyst was filtered off and the solvent removed under vacuum. The residue was picked up with aqueous 0.2N sodium hydroxide and kept for eight hours at 10° C. under nitrogen. After that, the solution was brought to pH 5 with acetic acid and left to stand for two hours at room temperature. The mixture was neutralized with aqueous sodium hydrogen carbonate and extracted with methylene chloride to give, after standard work up, the 11-amino deivative as free base. Treatment of which with methanolic hydrogen chloride afforded 0.15 g (yield 55%) of the title compound 2g. TLC on Kieselgel Plate (Merck $F_{254}$) solvent system: methylene chloride/methanol/acetic acid (80:20:1 by volume) Rf:0.23. m.p. 162°–164° C. (dec.) FD-MS: [M]+ 497

$^1$HNMR (200 MHz, DMSO $d_6$, 50° C.) δ: 1.23 (d, J=6.2 Hz, 3H, 5'-CH$_3$), 1.7–1.9 (m, 4H, 2'-CH$_2$, 3'-CH$_2$), 2.21 (m, 2H, 8-CH$_2$), 2.80 (m, 2H, 4'-H), 288 (m, 2H, 10-CH$_2$), 4.18 (dq, J=6.2, 9.5 Hz, 1H, 5'-H), 4.67 (m, 3H, COCH$_2$OH, COCH$_2$OH), 5.05 (m, 1H, 7-H), 5.28 (m, 1H, 1'-H), 5.31 (s, 1H, 9-OH), 7.88 (m, 2H, 2-H, 3-H), 8.27 (m, 2H, 1-H, 4-H), 8.18, 8.40 (two bm, 4H, 11-NH$_2$, 4'-NH$_2$).

EXAMPLE 12

Preparation of
4-demethoxy-6-deoxy-6-nitro-14-acetyl-adriamycinone (6f)

2 g (5 mmole) of 4-demethoxy-6-deoxy-6-nitro-daunomycinone (3f) was transformed into 1.7 g (yield 75.6%) of 14-acetyl derivative 6f following the procedure described in Example 5. TLC on Kieselgel Plate (Merck $F_{254}$) solvent system: methylene chloride/acetone (95:5 by volume) Rf:0.32. FD-MS: [M]+ 455

$^1$HNMR (200 MHz, CDCL$_3$) δ: 2.12 (dd, J=14.9, 4.8 Hz, 1H, 8ax-H), 2.20 (s, 3H, OCOCH$_3$), 2.53 (ddd, J=2.0, 2.4, 14.9 Hz, 1H, 8e-H), 3.15 (d, J=19.3 Hz, 1H, 10ax-H), 3.38 (dd, J=2.0, 19.3 Hz, 1H, 10e-H), 3.43 (m, 1H, 7-OH), 5.00 (m, 1H, 7-H), 5.15, 5.31 (two d, J=17.9 Hz, 2H, COCH$_2$OCO), 7.89 (m, 2H, 2-H, 3-H), 8.30 (m, 2H, 1-H, 4-H), 14.46 (s, 1H, 11-OH)

EXAMPLE 13

Preparation of
4-demethoxy-6-deoxy-6-nitro-9,14-orthoformate-3'-deamino-4'-deoxy-4'-epi-N-trifluoroacetyl-doxorubicin (9f)

1.7 g (3.7 mmole) of 4-demethoxy-6-deoxy-6-nitro-14-acetyladriamycinone (6f) was coupled with 1.6 g (6 mmole) of 1-chloro-2,3,4,6-tetradeoxy-4-(N-trifluoroacetamido)-L-erythro-hexopyranoside (4) in presence of silver trifluoromethanesulphonate as described in Example 1 to give 1 g (yield 41%) of N-trifluoroacetyl derivative 7f. TLC on Kieselgel Plate (Merck $F_{254}$) solvent system: methylene chloride/acetone (95:5 by volume) Rf:0.50. FD-MS: [M]+ 665

0.5 g (0.75 mmole) of compound 7f was treated with triethylorthoformate in presence of pyridinium p-toluensulfonate as described in Example 9 to afford, after chromatographic separation, 0.3 g (yield 60%) of the title compound 9f as mixture of two diastereoisomers with a molar ratio of 80/20. TLC on Kieselgel Plate (Merck $F_{254}$) solvent system: methylene chloride/acetone (95:5 by volume) Rf:0.65.

$^1$HNMR (220 MHz, CDCl$_3$) δ 1.1–1.3 (m, 6H, 5'-CH$_3$, OCH$_2$CH$_3$), 1.6–2.0 (m, 4H, 2'-CH$_2$, 3'-CH$_2$), 2.3–2.7 (m, 2H, 8-CH$_2$), 3.33 (s, 2H, 10--CH$_2$), 3.6–3.7 (m, 2H, OCH$_2$CH$_3$), 3.75 (m, 1H, 4'-H), 3.90 (dq, J=6.2, 9.5 Hz, 1H, 5'-H), 4.32, 4.45 (two d, J=17.4 Hz, COCH$_2$O major isomer), 4.20, 4.35 (two d, J=16.8 Hz, COCH$_2$O minor isomer), 4.87 (m, 1H, 1'-H), 5.01, 5.14 (dd, J=5.3, 5.3 Hz, 1H, 7-H major, 7-H minor), 5.70, 5.72 (s, 1H, CH-OCH$_2$CH$_3$ major, CH-OCH$_2$CH$_3$ minor), 6.04 (bd, J=9.0 Hz, 1H, NHCOCF$_3$), 7.85 (m, 2H, 2-H, 3-H), 8.27 (m, 2H, 1-H, 4-H), 13.52, 13.55 (s, 1H, 11-OH major, 11-OH minor)

EXAMPLE 14

Preparation of
4-demethoxy-6-deoxy-6-nitro-3'-deamino-4'-deoxy-4'-epi-amino doxorubicin hydrochloride (2f)

0.3 g (0.44 mmole) of compound 9f, prepared as described above, was dissolved in 200 ml of 0.2N aqueous sodium hydroxide and kept for ten hours at 0° C. under nitrogen. The solution was brought at pH 8.5 with acetic acid and extracted with methylene chloride. The aqueous solution was adjusted to pH 8.1 and extracted repeatedly with methylene chloride. The combined organic extracts, after being dried and concentrated to a small volume were acidified to pH 3.5 with anhydrous methanolic hydrogen chloride.

Upon addition of diethyl ether there was obtained 0.062 g (yield 25%) of the title compound 2f as hydrochloride salt. TLC on Kieselgel Plate (Merck $F_{254}$) solvent system: methylene chloride/methanol/acetic acid/water (30:4:1:0.5 by volume) Rf:0.30 m.p. 155°–157° C. (with dec.) MS-FD: [M]+ 527

$^1$HNMR (200 MHz, DMSO $d_6$) δ: 1.18 (d, J=6.3 Hz, 3H, 5'-CH$_3$), 1.6–1.9 (m, 4H, 2'-CH$_2$, 3'-CH$_2$), 2.1–2.5 (m, 2H, 8-CH$_2$), 2.84 (m, 1H, 4'-H), 3.01 (m, 2H, 10-CH$_2$), 4.06 (dq, J=6.3, 9.3 Hz, 1H, 5-H), 4.53 (m, 2H, CH$_2$OH), 5.07 (m, 1H, 7-H), 5.26 (m, 1H, 1'-H), 5.50 (m, 1H, CH$_2$OH), 7.88 (m, 2H, 2-H, 3-H), 8.14 (bs, 3H, 4'-NH$_3$+), 8.24 (m, 2H, 1-H), 4-H)

EXAMPLE 15

Preparation of
4-demethoxy-6-deoxy-6-amino-3'-deamino-4'-deoxy-4'-epi-amino-doxorubicin hydrochloride (2h)

0.15 g (0.22 mmole) of 9,14-orthoformate derivative 9f, prepared as described in Example 13, was dissolved in 150 ml of methanol and 15 ml of cyclohexene and treated with 0.15 g 10% Pd/C as described in Example 11 to give, upon addition with anhydrous methanolic hydrogen chloride, 0.02 g (yield 18.5%) of the 6-amino derivative 2h. TLC on Kieselgel Plate (Merck $F_{254}$) solvent system: methylene chloride/methanol/acetic acid/water (30:4:1:0.5 by volume ) Rf:0.22. MS-FD: [M]+ 497

$^1$HNMR (200 MHz, DMSO $d_6$, 50° C.) δ: 1.18 (d, J=6.3 Hz, 3H, 5'-CH$_3$), 1.6–1.9 (m, 4H, 2'-CH$_2$, 3'CH$_2$), 2.1–2.5 (m, 2H, 8-CH$_2$), 2.84 (m, 1H, 4'-H), 3.01 (m, 2H, 10-CH$_2$), 4.06 (bq, J=6.3, 9.3 Hz, 1H, 5-H), 4.53 (m, 2H, CH$_2$OH), 5.07 (m, 1H, 7-H), 5.26 (1H, 1'-H), 5.50 (m, 1H, CH$_2$OH), 7.88 (m, 2H, 2-H, 3-H), 8.14 (bs, 3H, 4'-NH$_3$+), 8.24 (m, 2H, 1-H, 4-H).

EXAMPLE 16

Preparation of
4-demethoxy-6-deoxy-6-nitro-3'-deamino-4'-deoxy-4'-epi-amino daunorubicin hydrochloride (1f)

0.78 g (1.76 mmole) of 4-demethoxy-6-deoxy-6-nitrodaunomycinone (3f) was coupled with 1-chloro-2,3,4,6-tetradeoxy-4-(N-trifluoroacetamido)-L-erythro-hexopyranoside (4) following the procedure described in Example 1 to afford 0.26 g (yield 62%) of the title compound 1f as hydrochloride salt.

TLC on Kieselgel plates (Merck F$_{254}$) solvent system: methylene chloride/methanol/acetic acid/water (80:20:7:3 by volume) Rf=0.42. MS-FD [M]+ 511

$^1$H NMR (200 MHz, DMSO-d$_6$) inter alia δ: 2.34 (s, 3H, COCH$_3$); 3.10 (d, J=18.7 Hz, 1H, 10ax-H); 3.27 (dd, J=1.8, 18.7 Hz, 1H 10eq-H), 5.11 (dd, J=2.3, 4.3 Hz, 1H, 7-H); 7.8–7.9 (m, 2H, 2-H, 3-H); 8.10 (bs, 3H, 4'-NH$_3$+); 8.2–8.4 (m, 2H, 1-H, 4-H); 13.55 (s, 1H, 11-OH).

EXAMPLE 17

Preparation of
4-demethoxy-6-deoxy-6-amino-3'-deamino-4'-deoxy-4'-epi-aminodaunorubicin hydrochloride (1h)

0.3 g (0.5 mmole) of compound 1f was dissolved in 200 ml of methanol and 20 ml of cyclohexene and treated with 0.2 g of 10% Pd/C. After refluxing for ten minutes, the catalyst was filtered off and solvent removed in vacuo. After crystallisation from methanol/ethyl ether, 0.2 g (Yield 76%) of the title compound 1h, as hydrochloride salt, was obtained. TLC on Kieselgel plates (Merck F$_{254}$) solvent system; methylene chloride/methanol/acetic acid/water (80:20:7:3 by volume) Rf=0.39. MS-FD: [M]+ 431

$^1$H NMR (200 MHz, DMSO-d$_6$) inter alia δ: 1.18 (d, J=6.3 Hz, 3H, 5'-CH$_3$); 1.6–1.9 (m, 4H, 2'-CH$_2$, 3'-CH$_2$); 2.1–2.5 (m, 2H, 8-CH$_2$); 2.84 (m, 1H, 4'-H); 3.01 (m, 2H, 10-CH$_2$); 4.06 (bq, J=6.3, 9.3 Hz, 1H, 5-H); 5.7 (m, 1H, 7-H); 5.26 (m, 1H, 1'-H); 7.8–7.9 (m, 2H, 2-H, 3-H); 8.10 (bs, 3H, 4'-NH$_3$+); 8.2–8.4 (m, 2H, 1-H, 4-H).

EXAMPLE 18

Preparation of
4-demethoxy-11-deoxy-11-nitro-3'-deamino-4'-deoxy-4'-epi-amino-daunorubicin hydrochloride (1e)

0.58 g (1.46 mmole) of 4-demethoxy-11-deoxy-11-nitrodaunomycinone (3e) was coupled with sugar (4) following the procedure described in Example 1 to afford, after usual work up, 0.5 g (yield 61%) of the title compound 1e as hydrochloride salt.

TLC on Kieselgel plates (Merck F$_{254}$) solvent system: methylene chloride/methanol/acetic acid/water (80:20:7:3 by volume) Rf=0.44. MS-FD [M]+ 511 $^1$H NMR (200 MHz, DMSO-d$_6$) inter alia δ: 1.18 (d, J=6.3 Hz, 3H, 5'-CH$_3$); 1.6–1.8 (m, 4H, 2'-CH$_2$, 3'-CH$_2$); 2.1–2.5 (m, 2H, 8-CH$_2$); 2.37 (s, 3H, COCH$_3$); 3.07 (m, 2H, 10-CH$_2$); 4.06 (bq, J=6.3, 9.3 Hz, 1H, 5'-H); 5.03 (m, 1H, 7-H); 5.32 (m, 1H, 1'-H); 7.8–7.9 (m, 2H, 2-H, 3-H); 8.10, bs, 3H, 4'-NH$_3$+); 8.2–8.4 (m, 2H, 1H, 4H), 13.7 (s, 1H, 6-OH).

EXAMPLE 19

Preparation of
4-demethoxy-11-deoxy-11-amino-3'-deamino-4'-deoxy-4'-epiaminodaunorubicin hydrochloride (1g)

0.2 g (0.36 mmole) of compound 1e was transformed into its reduced amino derivative 1g, following the procedure described in Example 17.

Yield 80%.

TLC on Kieselgel plates (Merck F$_{254}$) solvent system: methylene chloride/methanol/acetic acid/water (80:20:7:3 by volume) Rf=0.41. MS-FD [M]+ 481.

We claim:

1. An anthracycline glycoside of formula 1 or 2:

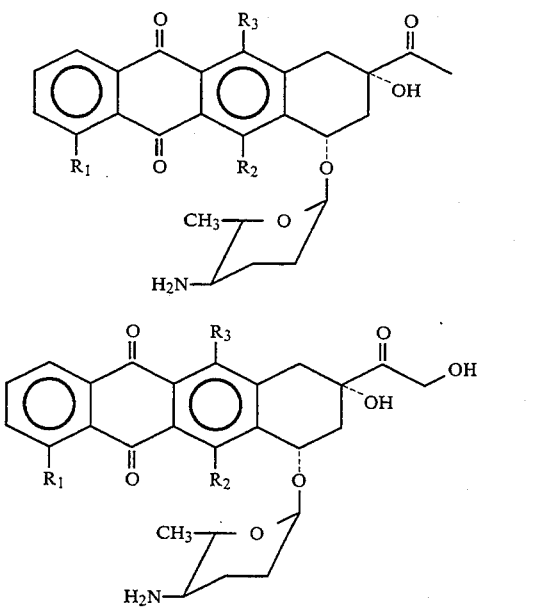

wherein R$_1$ is selected from the group consisting of hydrogen, fluorine, hydroxy and amino; R$_2$ and R$_3$ both represent hydroxy or one of R$_2$ and R$_3$ is hydrogen, nitro or amino and the other of R$_2$ and R$_3$ is hydroxy; or a pharmaceutically acceptable acid addition salt thereof.

2. A compound according to claim 1, which is selected from the group consisting of 4-demethyl-3'-deamino-4'-deoxy-4'-epi-amino-daunorubicin and its hydrochloride; 4-demethoxy-4-amino-3'-deamino-4'-deoxy-4'-epi-amino-daunorubicin and its hydrochloride; and 4-demethoxy-4-fluoro-3'-deamino-4'-deoxy-4'-epi-amino daunorubicin and its hydrochloride.

3. A compound according to claim 1, which is selected from the group consisting of 4-demethyl-3'-deamino-4'-deoxy-4'-epi-amino-doxorubicin and its hydrochloride; 4-demethyl-6-deoxy-3'-deamino-4'-deoxy-4'-epi-amino-doxorubicin and its hydrochloride; 4-demethoxy-11-deoxy-11-nitro-3'-deamino-4'-deoxy-4'-epi-amino-doxorubicin and its hydrochloride; 4-demethoxy-11-deoxy-11-amino-3'-deamino-4'-deoxy-4'-epi-amino-doxorubicin and its hydrochloride; 4-demethoxy-6-deoxy-6-nitro-3'-deamino-4'-deoxy-4'-epi-amino-doxorubicin and its hydrochloride; and 4-demethoxy-6-deoxy-6-amino-3'-deamino-4'-epi-amino-doxorubicin and its hydrochloride.

4. A compound of formula:

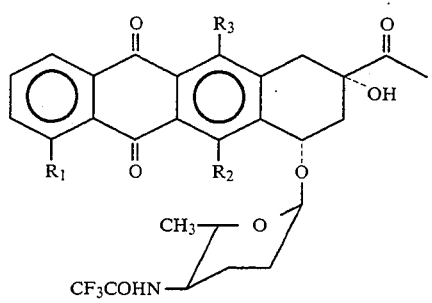

wherein R₁ is selected from the group consisting of hydrogen, fluorine, hydroxy and amino; R₂ and R₃ both represent hydroxy or one of R₂ and R₃ is hydrogen or nitro and the other of R₂ and R₃ is hydroxy.

5. A compound of formula:

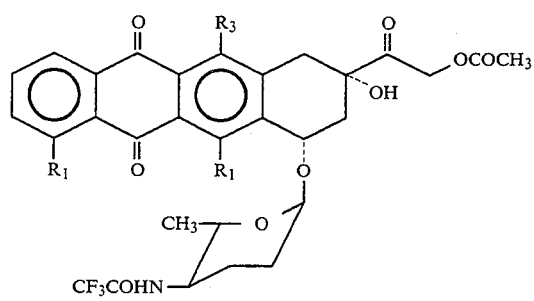

or

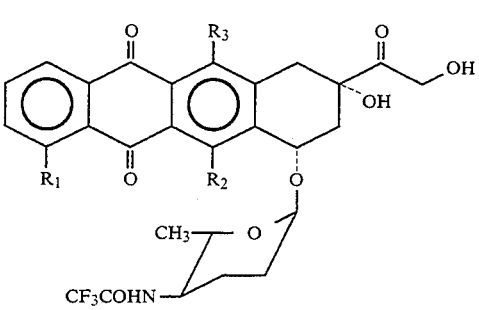

or wherein in each formula:
R₁ is selected from the group consisting of hydrogen, fluorine, hydroxy and amino;
R₂ and R₃ both represent hydroxy or one of R₂ and R₃ is hydrogen or nitro and the other of R₂ and R₃ is hydroxy.

* * * * *